US008202892B2

(12) United States Patent
Huchel et al.

(10) Patent No.: US 8,202,892 B2
(45) Date of Patent: Jun. 19, 2012

(54) ADVANCED GLYCATION END PRODUCTS AS ACTIVE INGREDIENTS

(75) Inventors: Ursula Huchel, Köln (DE); Christian Kropf, Hilden (DE); Thomas Welss, Duesseldorf (DE); Melanie Giesen, Geldern (DE); Andreas Bock, Duesseldorf (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 228 days.

(21) Appl. No.: 12/683,821

(22) Filed: Jan. 7, 2010

(65) Prior Publication Data

US 2010/0204176 A1 Aug. 12, 2010

Related U.S. Application Data

(63) Continuation of application No. PCT/EP2008/058255, filed on Jun. 27, 2008.

(30) Foreign Application Priority Data

Jul. 10, 2007 (DE) .......................... 10 2007 032 393

(51) Int. Cl.
*A61K 31/44* (2006.01)
(52) U.S. Cl. ................ 514/348; 8/94.16; 8/161; 424/73
(58) Field of Classification Search .................... 514/348
See application file for complete search history.

(56) References Cited

U.S. PATENT DOCUMENTS

| 4,032,676 | A | 6/1977 | Heins et al. |
| 4,865,774 | A | 9/1989 | Fabry et al. |
| 4,931,218 | A | 6/1990 | Schenker et al. |
| 5,294,726 | A | 3/1994 | Behler et al. |
| 6,218,435 | B1 | 4/2001 | Henry et al. |
| 6,235,913 | B1 | 5/2001 | Raths et al. |
| 6,419,937 | B1 | 7/2002 | Waldmann-Laue et al. |
| 2004/0076597 | A1 | 4/2004 | Berens et al. |
| 2007/0059264 | A1* | 3/2007 | Ahluwalia et al. .............. 424/66 |

FOREIGN PATENT DOCUMENTS

| DE | 198 16 665 A1 | 10/1999 |
| DE | 101 60 966 A1 | 6/2003 |
| WO | 03/051419 A1 | 6/2003 |
| WO | 03089601 A2 | 10/2003 |
| WO | 2005051288 A2 | 6/2005 |

* cited by examiner

*Primary Examiner* — Sharmila G. Landau
*Assistant Examiner* — Barbara Frazier
(74) *Attorney, Agent, or Firm* — David P. LeCroy

(57) ABSTRACT

Cosmetic composition comprising at least one compound from advanced glycation end products ('AGEs') and/or precursors thereof as an agent for skin treatment, especially for protection and/or care of the skin. The present invention further provides a cosmetic composition comprising at least one compound from the group of the AGEs and/or precursors thereof, wherein the AGEs are prepared by reacting sugars with the amino acids lysine and/or arginine.

6 Claims, No Drawings

ADVANCED GLYCATION END PRODUCTS AS ACTIVE INGREDIENTS

CROSS REFERENCE TO RELATED APPLICATIONS

The present application is a continuation of International Patent Application No. PCT/EP2008/058255, filed 27 Jun. 2008, which claims priority to German Patent Application No. 10 2007 032 393.1, filed 10 Jul. 2007.

The present invention relates to the use of a cosmetic composition comprising at least one compound from the group of AGEs (advanced glycation end products) and/or their precursors as an agent for skin treatment, especially for protecting and/or caring for skin.

As the largest human organ, human skin performs numerous vital functions. With a surface area of approximately 2 m² for adults, skin plays a prominent role as a protection and sensory organ. The task of this organ is to communicate and fend off mechanical, thermal, actinic, chemical and biological stimuli. Moreover, it plays an important role as the regulatory and target organ in human metabolism.

Cosmetic treatment of skin is therefore an important component of human body care. One aim of skin care in the cosmetic sense is to reinforce or restore the natural function of the skin as a barrier against aging and environmental effects and against the loss of autologous substances (e.g., water, natural fats, electrolytes), and to slow down the natural aging process.

Aging and environmental effects, such as excessive electromagnetic radiation (exposure to UV- and IR radiation), gases, heavy metals, dust or carbon black particles or oxidative stress are often responsible for sustained damage to the biological functionality of skin.

Consequently, particularly interesting cosmetic active ingredients for the treatment of skin are those that impart conditioning, protection and revitalizing properties against signs of aging. Skin care and skin protection preparations comprising a whole range of different cosmetic active ingredients are available in large numbers and in many forms.

Nevertheless there is still the need to enrich the prior art with novel cosmetic active ingredients or complexes of active ingredients. In particular, those active ingredients that provide a sustained protection and/or an improved skin care are of great interest.

In this context, German Patent Application Publication No. DE 100 41 482 A1 discloses "AGEs" (advanced glycation end products) as cosmetic active ingredients for the induction and intensification of tanning mechanisms of human skin and the use of one or more substances from the group of AGEs and/or their precursors for increasing the melanin synthesis of the skin.

German Patent Application Publication No. DE 101 60 966 A1 teaches a hair dye comprising at least one compound from the group of AGEs, their synthetic precursors and/or the lipofuscins and the use of this type of hair dye for increasing the melanin synthesis in the hair root and the storage of melanin in hair.

It is common to both publications that cosmetic active ingredients from the group of the AGEs are used to increase the melanin synthesis in hair and/or of skin. Any indication to other or further biologically relevant effects of the AEG could not be found in either document.

It has now been surprisingly found that compounds from the group of AGEs and/or their precursors can also be used as skin treatment agents, especially for protecting and/or for nurturing skin.

Accordingly, the subject matter of the present invention includes use of a cosmetic composition comprising at least one compound from the group of AGEs and/or their precursors as an agent for skin treatment, especially for protecting and/or caring for skin.

Another subject matter of the present invention includes a process for treating skin, especially for protecting and/or caring for skin, wherein a cosmetic composition for protecting and/or for caring for skin is topically applied onto the skin.

Likewise, the subject matter of the present invention includes use of a cosmetic composition comprising at least one compound from the group of advanced glycation end products (AGEs)
- for the non-therapeutic increase of energy metabolism, preferably for the increase of the ATP synthesis rate in skin cells,
- for the non-therapeutic inhibition of cell division activity of skin cells, and/or
- for the non-therapeutic inhibition of inflammation reactions of the skin.

In addition, a subject matter of the present invention includes a cosmetic composition comprising at least one compound from the group of lysine- and/or arginine-based AGEs and/or their precursors, wherein the lysine- and/or arginine-based AGEs and/or their precursors are synthesized by reacting sugars, preferably glucose, lactose, galactose and/or mannose, especially glucose and/or lactose, with the amino acids lysine and/or arginine.

In a preferred embodiment, the above-cited cosmetic composition comprises an emulsifier or surfactant as a further component, preferably selected from the group of anionic, cationic, amphoteric and/or non-ionic surfactants or emulsifiers or from their mixtures.

The cosmetic composition particularly preferably comprises at least one additional component selected from the group of cosmetic active ingredients, vitamins, protein hydrolyzates, film-forming substances, UV-filter substances, fragrances, conditioning agent active ingredients, thickeners, conservation agents, antioxidants, colorants, buffers, sequestrants, propellants, reducing agents, anti-dandruff active ingredients, tanning agents, moisturizers for the skin and/or lustering agents.

Another subject matter of the present invention includes a process for treating skin, especially for protecting and/or caring for skin, wherein the above-cited cosmetic composition is topically applied onto the skin.

Another subject matter of the present invention includes the use of at least one compound from the group of advanced glycation end products (AGEs) and/or their precursors for manufacturing a cosmetic composition and/or a medicament
- for increasing the energy metabolism, preferably for increasing the ATP synthesis rate in skin cells,
- for the inhibition of cell division activity of skin cells, and/or
- for the treatment of inflammation reactions of the skin.

According to the invention the generally used term, "skin" is understood to mean the skin itself, the mucosa as well as the skin adnexa, in so far that they include living cells, particularly hair follicles, hair roots, hair bulbs, the ventral epithelial layer of the nail bed (lectulus), as well as sebaceous glands and perspiratory glands. In the context of the invention, the generally used term "skin" is preferably understood to mean the "human skin".

As previously noted, the abbreviation AGE refers to the English phrase "advanced glycation end products". In the context of the present invention, AGEs may be obtained according to the following (exemplary) reaction equation:

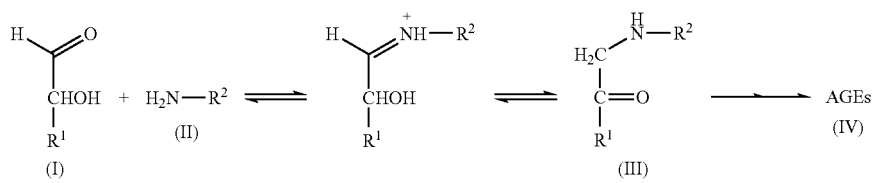

In the context of the present invention, advantageously useful in addition to the actual AGEs are also their precursors, such as Amadori or Maillard products (corresponding to (III) in the above reaction equation) or "EGEs" (early glycation end products), obtainable as intermediate products in the rearrangement of the Amadori products (III) to AGEs (IV).

Further products of the Maillard reaction, in particular, those which also derive from the Amadori product such as maltol (Larixin, 3-hydroxy-2-methyl-4H-pyran-4-one) and 4-hydroxy-2,5-dimethyl-3(2H)-furanone (Furaneol®), can likewise be included under the term, "precursor".

In the context of the present invention, the term, "precursor" is explicitly understood not to include the relevant starting materials of the reaction (i.e., unreacted educts). Advantageous starting materials (I) possess an aldehyde group (CHO) and are chosen, for example, from sugars (aldoses, e.g., trioses, tetroses, pentoses, hexoses and the like, such as glucose, galactose, mannose, etc.). Advantageous starting materials (II) possess a free amino group and are chosen, for example, from amino acids and from peptides having terminal amino groups. In particular, lysine, hydroxylysine, arginine, tryptophan and histidine are advantageous. Further advantageously, the free amino group can also be derived from N-terminal ends of proteins and peptides; also advantageous are sphingosine as well as dihydrosphingosine and their homologs with differently sized (unsaturated) acyl groups. AGEs according to the invention preferably comprise at least one nitrogen-containing and/or oxygen-containing five and/or six-member ring.

In the context of the present invention, furan derivatives FFI 1 and furanone 2, for example, corresponding to the following structural formulas, are also advantageous:

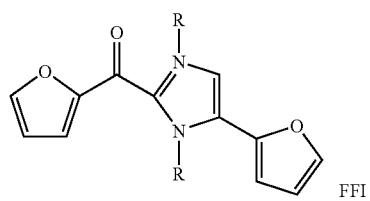

FFI 1

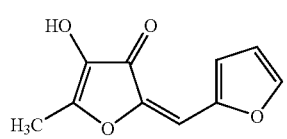

2

In the context of the present invention, "AFGP" is also advantageous and corresponds to the following structural formula 3:

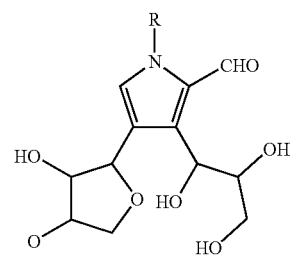

3

In the context of the present invention, pyrralines are also advantageous and correspond, for example, to the following structural formula 4:

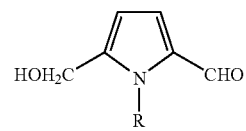

4

In the context of the present invention, pyrano pyranones are also advantageous and correspond, for example, to the following structural formula 5:

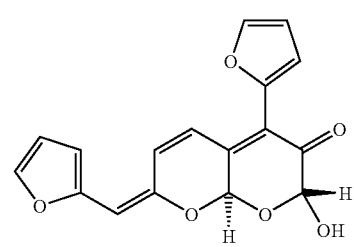

5

In the context of the present invention, pyrrolinones are also advantageous and correspond, for example, to the following structural formulas:

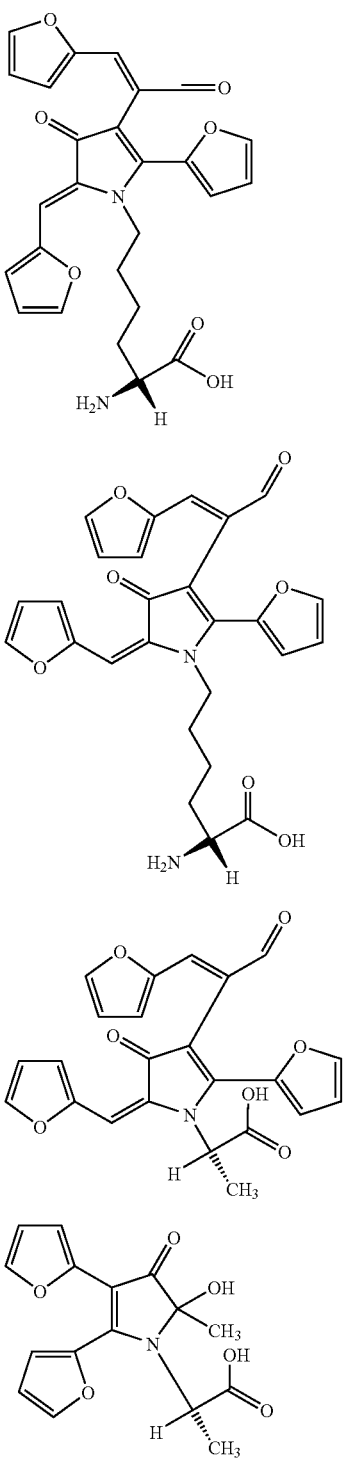

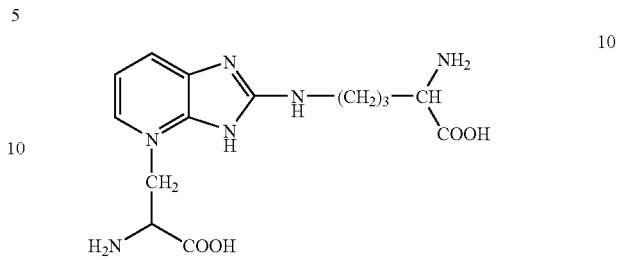

In the context of the present invention, pentosidine 10 is also advantageous and corresponds to the following structural formula:

In the context of the present invention, the "A2E" 11 is also particularly advantageous and corresponds to the following structural formula:

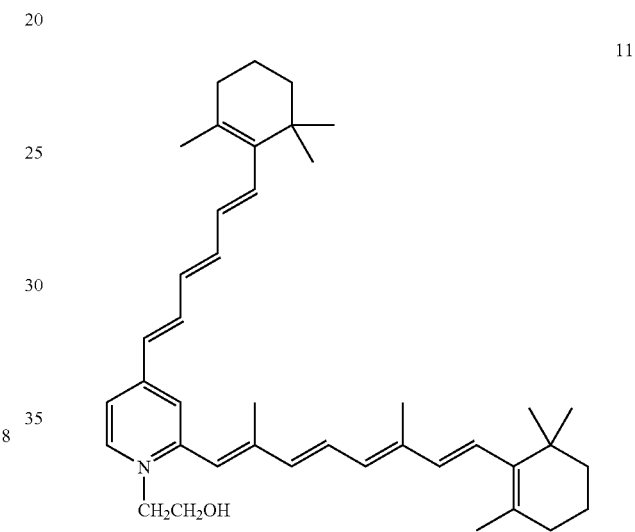

According to the invention, the R group in structural formulas 1, 3 and 4 advantageously derive from proteins and peptides; accordingly, said groups are peptide, amino acid or protein groups which can be linked through an end group or a side group to the nitrogen atom.

Furthermore, R is advantageously chosen, for example, from the group of saturated or unsaturated, branched or unbranched alkyl groups containing 1 to 35 carbon atoms.

Of course, the illustrated structural formulas should not limit the invention to certain isomers of the inventive substances. In fact, in the context of the present invention, non-illustrated isomers or isomer mixtures are also advantageous.

The illustrated advanced glycation end products (AGES), obtained by treating at least one compound from the group of the sugars with at least one compound from the group of the amino acids, and/or their precursors are additionally preferred, wherein the molar ratio of sugar to amino acid in the reaction is preferably between 10:1 and 1:1, particularly preferably between 7:1 and 1:1 and in particular between 5:1 or 4:1.

Further preferred advanced glycation end products (AGEs) and/or their precursors are obtained by treating an amino acid selected from lysine, hydroxylysine, arginine, tryptophan and/or histidine.

Further preferred advanced glycation end products (AGEs) and/or their precursors are obtained by treating an aldose, preferably selected from glucose, lactose, galactose and/or mannose.

Likewise preferred are lysine- and/or arginine-based advanced glycation end product (AGEs) and/or their precursors, which are formed by treating sugars, preferably glucose, lactose, galactose and/or mannose, in particular, glucose and/or lactose, with the amino acids lysine and/or arginine, preferably at reaction temperatures of 15° C. to 95° C. The reaction products that are formed in reactions in the temperature ranges between 16° C. and 35° C., between 36° C. and 50° C., between 51° C. and 75° C. or between 76° C. and 95° C., in particular at 15° C., 20° C., 25° C., 30° C., 35° C., 40° C., 45° C., 50° C., 55° C., 60° C., 65° C., 70° C., 75° C., 80° C., 85° C., 90° C. or 95° C., are particularly preferred.

Likewise preferred are lysine- and/or arginine-based advanced glycation end products (AGEs) and/or their precursors which are formed by treating sugars, preferably glucose, lactose, galactose and/or mannose, in particular glucose and/or lactose, with the amino acids lysine and/or arginine, for reaction times of 0.5 hour (hr) to 48 hr. The reaction products that are formed after reaction times between 0.5 hr and 2 hr, between 1 hr and 4 hr, between 1 hr and 8 hr, between 4 hr and 16 hr and/or between 12 hr and 24 hr, in particular of 0.5 hr, 1 hr, 2 hr, 3 hr, 4 hr, 5 hr, 6 hr, 7 hr, 8 hr, 9 hr, 10 hr, 11 hr, 12 hr, 13 hr, 14 hr, 15 hr, 16 hr, 17 hr, 18 hr, 19 hr, 20 hr, 21 hr, 22 hr, 23 hr or 24 hr, are particularly preferred.

In principle, combinations of each of the above cited reaction temperatures with each of the cited reaction times are preferred.

A quite particularly reaction condition is the reaction of sugars, preferably glucose, lactose, galactose and/or mannose, in particular glucose and/or lactose, with the amino acids lysine and/or arginine at about 15° C. with reaction times of about 0.5 hr, 1 hr, 2 hr, 3 hr, 4 hr, 5 hr, 6 hr, 7 hr, 8 hr, 9 hr, 10 hr, 11 hr, 12 hr, 13 hr, 14 hr, 15 hr, 16 hr, 17 hr, 18 hr, 19 hr, 20 hr, 21 hr, 22 hr, 23 hr or 24 hr, at about 20° C. with reaction times of about 0.5 hr, 1 hr, 2 hr, 3 hr, 4 hr, 5 hr, 6 hr, 7 hr, 8 hr, 9 hr, 10 hr, 11 hr, 12 hr, 13 hr, 14 hr, 15 hr, 16 hr, 17 hr, 18 hr, 19 hr, 20 hr, 21 hr, 22 hr, 23 hr or 24 hr, at about 25° C. with reaction times of about 0.5 hr, 1 hr, 2 hr, 3 hr, 4 hr, 5 hr, 6 hr, 7 hr, 8 hr, 9 hr, 10 hr, 11 hr, 12 hr, 13 hr, 14 hr, 15 hr, 16 hr, 17 hr, 18 hr, 19 hr, 20 hr, 21 hr, 22 hr, 23 hr or 24 hr, at about 25° C. with reaction times of about 0.5 hr, 1 hr, 2 hr, 3 hr, 4 hr, 5 hr, 6 hr, 7 hr, 8 hr, 9 hr, 10 hr, 11 hr, 12 hr, 13 hr, 14 hr, 15 hr, 16 hr, 17 hr, 18 hr, 19 hr, 20 hr, 21 hr, 22 hr, 23 hr or 24 hr, at about 30° C. with reaction times of about 0.5 hr, 1 hr, 2 hr, 3 hr, 4 hr, 5 hr, 6 hr, 7 hr, 8 hr, 9 hr, 10 hr, 11 hr, 12 hr, 13 hr, 14 hr, 15 hr, 16 hr, 17 hr, 18 hr, 19 hr, 20 hr, 21 hr, 22 hr, 23 hr or 24 hr, at about 30° C. with reaction times of about 0.5 hr, 1 hr, 2 hr, 3 hr, 4 hr, 5 hr, 6 hr, 7 hr, 8 hr, 9 hr, 10 hr, 11 hr, 12 hr, 13 hr, 14 hr, 15 hr, 16 hr, 17 hr, 18 hr, 19 hr, 20 hr, 21 hr, 22 hr, 23 hr or 24 hr, at about 35° C. with reaction times of about 0.5 hr, 1 hr, 2 hr, 3 hr, 4 hr, 5 hr, 6 hr, 7 hr, 8 hr, 9 hr, 10 hr, 11 hr, 12 hr, 13 hr, 14 hr, 15 hr, 16 hr, 17 hr, 18 hr, 19 hr, 20 hr, 21 hr, 22 hr, 23 hr or 24 hr, at about 40° C. with reaction times of about 0.5 hr, 1 hr, 2 hr, 3 hr, 4 hr, 5 hr, 6 hr, 7 hr, 8 hr, 9 hr, 10 hr, 11 hr, 12 hr, 13 hr, 14 hr, 15 hr, 16 hr, 17 hr, 18 hr, 19 hr, 20 hr, 21 hr, 22 hr, 23 hr or 24 hr, at about 45° C. with reaction times of about 0.5 hr, 1 hr, 2 hr, 3 hr, 4 hr, 5 hr, 6 hr, 7 hr, 8 hr, 9 hr, 10 hr, 11 hr, 12 hr, 13 hr, 14 hr, 15 hr, 16 hr, 17 hr, 18 hr, 19 hr, 20 hr, 21 hr, 22 hr, 23 hr or 24 hr, at about 50° C. with reaction times of about 0.5 hr, 1 hr, 2 hr, 3 hr, 4 hr, 5 hr, 6 hr, 7 hr, 8 hr, 9 hr, 10 hr, 11 hr, 12 hr, 13 hr, 14 hr, 15 hr, 16 hr, 17 hr, 18 hr, 19 hr, 20 hr, 21 hr, 22 hr, 23 hr or 24 hr, at about 55° C. with reaction times of about 0.5 hr, 1 hr, 2 hr, 3 hr, 4 hr, 5 hr, 6 hr, 7 hr, 8 hr, 9 hr, 10 hr, 11 hr, 12 hr, 13 hr, 14 hr, 15 hr, 16 hr, 17 hr, 18 hr, 19 hr, 20 hr, 21 hr, 22 hr, 23 hr or 24 hr, at about 60° C. with reaction times of about 0.5, 1 hr, 2 hr, 3 hr, 4 hr, 5 hr, 6 hr, 7 hr, 8 hr, 9 hr, 10 hr, 11 hr, 12 hr, 13 hr, 14 hr, 15 hr, 16 hr, 17 hr, 18 hr, 19 hr, 20 hr, 21 hr, 22 hr, 23 hr or 24 hr, at about 65° C. with reaction times of about 0.5 hr, 1 hr, 2 hr, 3 hr, 4 hr, 5 hr, 6 hr, 7 hr, 81 hr, 9 hr, 10 hr, 11 hr, 12 hr, 13 hr, 14 hr, 15 hr, 16 hr, 17 hr, 18 hr, 19 hr, 20 hr, 21 hr, 22 hr, 23 hr or 24 hr, at about 70° C. with reaction times of about 0.5 hr, 1 hr, 2 hr, 3 hr, 4 hr, 5 hr, 6 hr, 7 hr, 8 hr, 9 hr, 10 hr, 11 hr, 12 hr, 13 hr, 14 hr, 15 hr, 16 hr, 17 hr, 18 hr, 19 hr, 20 hr, 21 hr, 22 hr, 23 hr or 24 hr, at about 75° C. with reaction times of about 0.5 hr, 1 hr, 2 hr, 3 hr, 4 hr, 5 hr, 6 hr, 7 hr, 8 hr, 9 hr, 10 hr, 11 hr, 12 hr, 13 hr, 14 hr, 15 hr, 16 hr, 17 hr, 18 hr, 19 hr, 20 hr, 21 hr, 22 hr, 23 hr or 24 hr, at about 80° C. with reaction times of about 0.5 hr, 1 hr, 2 hr, 3 hr, 4 hr, 5 hr, 6 hr, 7 hr, 8 hr, 9 hr, 10 hr, 11 hr, 12 hr, 13 hr, 14 hr, 15 hr, 16 hr, 17 hr, 18 hr, 19 hr, 20 hr, 21 hr, 22 hr, 23 hr or 24 hr, at about 85° C. with reaction times of about 0.5 hr, 1 hr, 2 hr, 3 hr, 4 hr, 5 hr, 6 hr, 7 hr, 8 hr, 9 hr, 10 hr, 11 hr, 12 hr, 13 hr, 14 hr, 15 hr, 16 hr, 17 hr, 18 hr, 19 hr, 20 hr, 21 hr, 22 hr, 23 hr or 24 hr, at about 90° C. with reaction times of about 0.5 hr, 1 hr, 2 hr, 3 hr, 4 hr, 5 hr, 6 hr, 7 hr, 8 hr, 9 hr, 10 hr, 11 hr, 12 hr, 13 hr, 14 hr, 15 hr, 16 hr, 17 hr, 18 hr, 19 hr, 20 hr, 21 hr, 22 hr, 23 hr or 24 hr, at about 95° C. with reaction times of about 0.5 hr, 1 hr, 2 hr, 3 hr, 4 hr, 5 hr, 6 hr, 7 hr, 8 hr, 9 hr, 10 hr, 11 hr, 12 hr, 13 hr, 14 hr, 15 hr, 16 hr, 17 hr, 18 hr, 19 hr, 20 hr, 21 hr, 22 hr, 23 hr or 24 hr.

In regard to the reaction times, the term means, for example, that the actual reaction times can vary from the given reaction times by up to 20 minutes.

In regard to the reaction temperatures, the term means, for example, that the actual reaction temperature can vary from the given reaction temperature by up to 3° C.

A preferred solvent for the synthesis of the inventive AGEs is water, preferably adjusted with a phosphate mixture as the buffer to a pH between 3.0 and 10.0, preferably to 3.0, 4.0, 5.0, 6.0, 7.0, 8.0, 9.0 or 10.0, in particular to 7.0. A preferred process for synthesizing the inventive AGEs is the reaction of at least one sugar with at least one amino acid in an aqueous buffer solution. The volume of solvent is subsequently reduced and the product isolated, preferably by freeze drying.

Preferred inventive lysine-based AGEs and/or their precursors include products of the Maillard reaction of lysine A with sugars. Examples of such inventive substances include N-ε-fructosyllysine (fructoselysine) 12, N-ε-carboxymethyllysine (CML) 13, carboxyethyllysine (CEL) 14 or maltosine 15 as well as pyridosine 15a, corresponding to the following structural formulas:

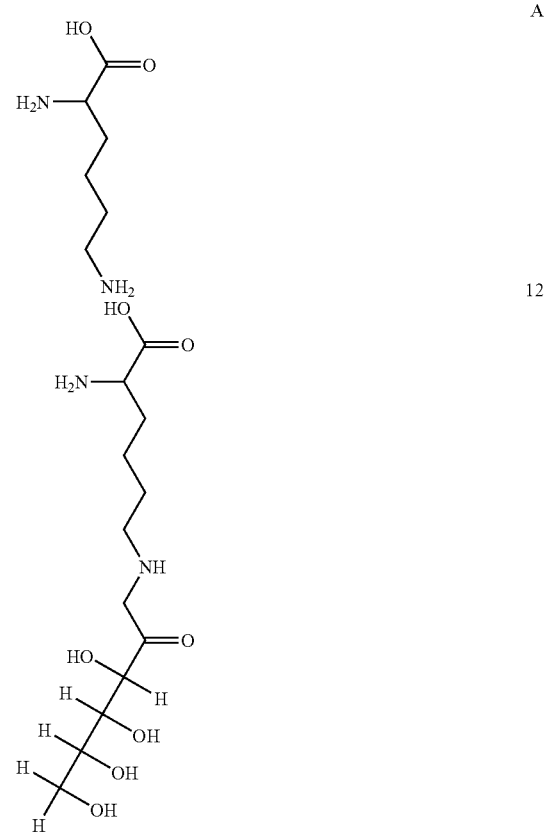

-continued
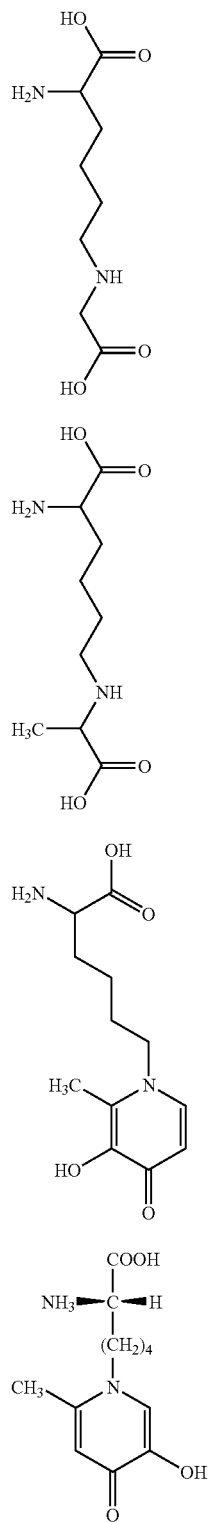
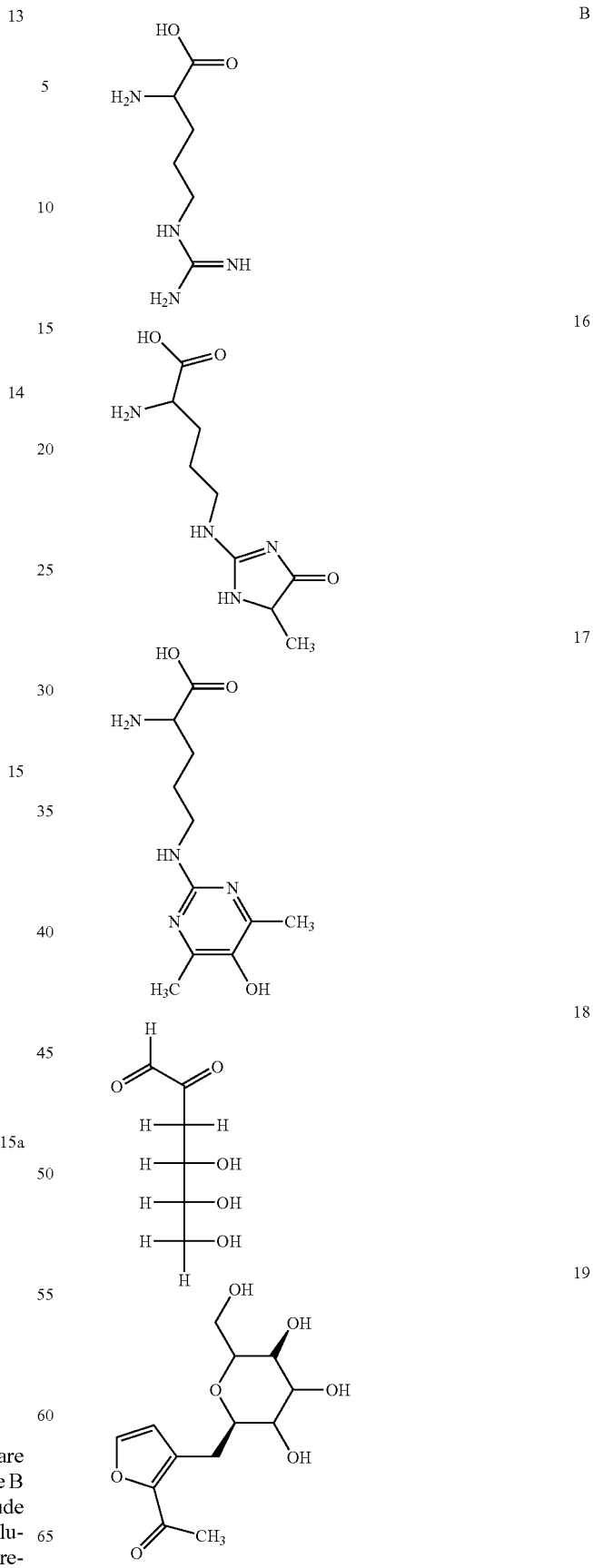
Further preferred inventive arginine-based AGEs that are comprised are products of the Maillard reaction of arginine B with sugars. Examples of such inventive substances include ornithinoimidazolinone 16, argpyrimidine 17, 3-desoxyglucosulose (3-DG) 18 or galactosylisomaltol 19, which correspond to the following structural formulas:

In the context of the present invention, glycation products of lysine and arginine are also advantageous. Examples of such products include CML 20, CEL 21, pyrraline 22, DOLD 23, GOLD 24, MOLD 25, pentosidine 26, dihydroxyimidazolidine 27, glarg 28, CMA 29, GO-imidazolone 30, MGO-imidazolone 31, 3-DG-imidazolone 32 or argopyrimidine 33, which correspond to the following structural formulas:
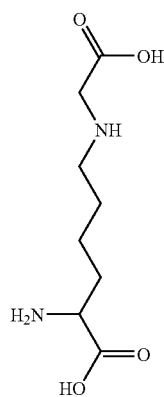
20
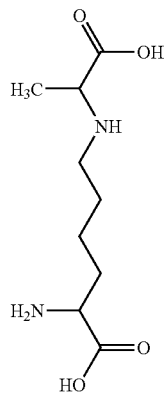
21
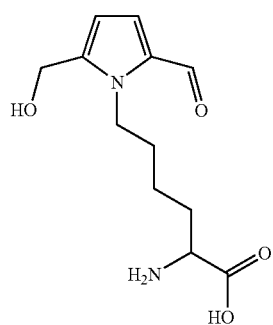
22
-continued
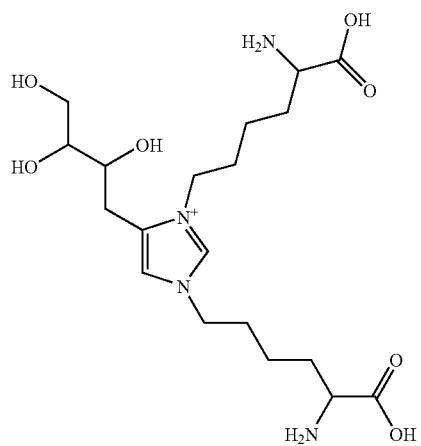
23
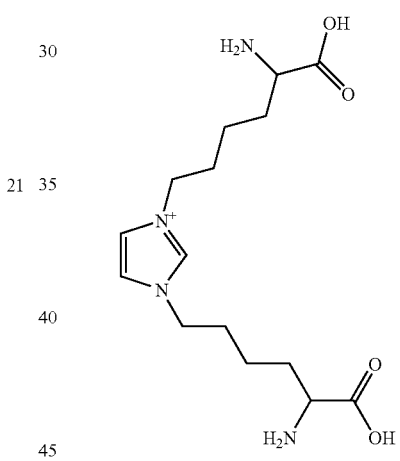
24
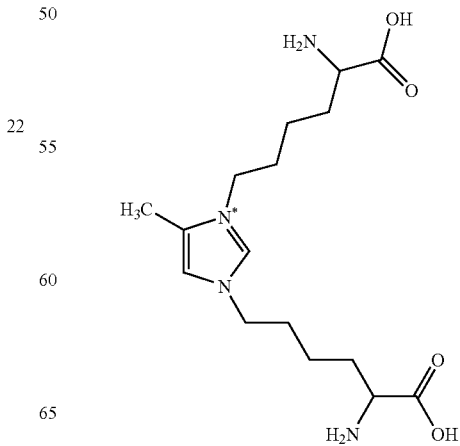
25

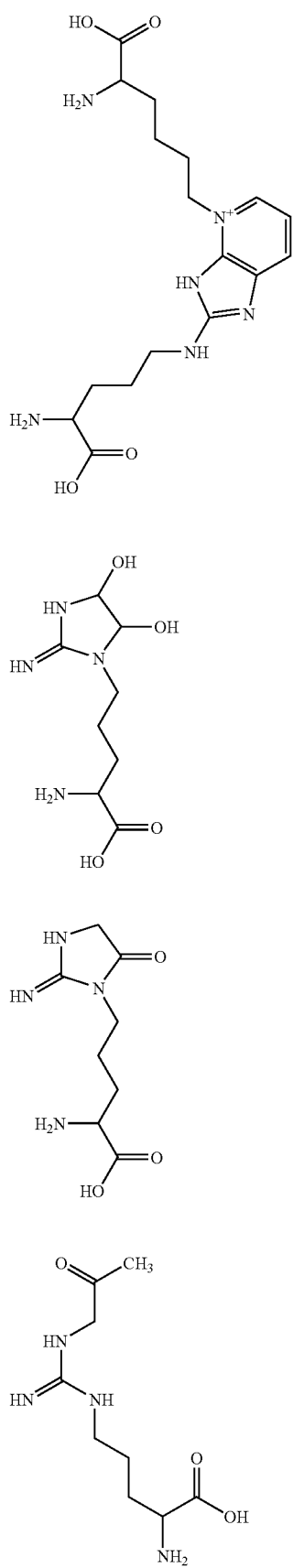
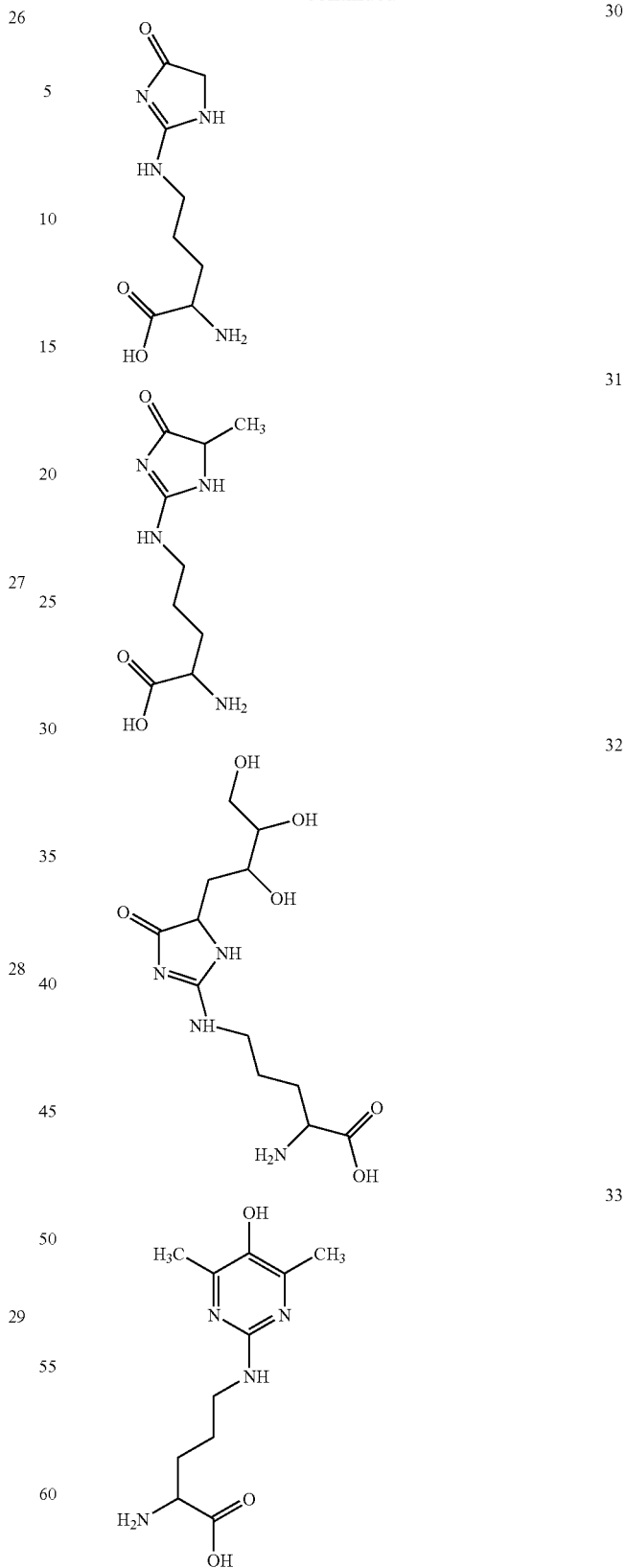
A preferred embodiment of the invention is the use of an inventive cosmetic composition containing a compound or a mixture of different compounds from the group AGEs and/or of their precursors in an amount of 0.00001 to 15 wt. %, preferably 0.0001 to 5 wt. %, particularly preferably 0.001 to 1 wt. %, each based on the total composition.

The cosmetic and pharmaceutical potential of the inventive group of AGEs (advanced glycation end products) and/or their precursors can be attributed to a series of most advantageous and surprising effects of these substances, which will be described in more detail below.

ATP (adenosine triphosphate) is the universal storage form for chemical energy in cells. ADP and $P_i$ (inorganic phosphate) are formed by cleavage of the distal phosphate group. This reaction is strongly exergonic (i.e., energy releasing). ATP is produced by the cellular, oxidative decomposition of fats, carbohydrates and proteins. ATP serves the skin cells and thereby also the biologically active hair follicle cells as an energy supplier for biochemical syntheses and transport processes. These processes are endergonic (i.e. they only occur under energy input). In order to optimally sustain and renew their metabolism and cellular structures, cells are therefore reliant on an adequate supply of ATP. For example, dermal papillae cells need ATP for the production of growth factors and therewith the control of the hair cycle. The proliferation and differentiation of hair shaft keratinocytes is likewise coupled to the ATP synthesis as the biosynthesis of specific proteins is an essential requirement for both processes. If the ATP synthesis rate of the cells that are relevant to hair can be increased, then more energy is available to the cells in order to sustain metabolic processes and cellular structures, and in order to renew structures (e.g., for repair processes or the new growth of hair). Consequently, an adequate supply of ATP to the skin is an essential requirement for a healthy skin and strong or vital hair.

In the context of the present invention it was determined that the energy metabolism, in particular, the ATP synthesis rate in skin cells, can be augmented by adding a composition comprising at least one compound from the group of the AGEs and/or their precursors (see Example 3). Accordingly, especially for environmentally damaged skin cells or age-related weakened skin cells, the energy supply of the respective cells can be maintained or increased, thereby strengthening or vitalizing the biologically active cells.

Accordingly, a preferred subject matter of the present invention is the use of a cosmetic composition comprising at least one compound from the group of the AGEs and/or their precursors
- for vitalizing and/or revitalizing the skin,
- for accelerating the regeneration of stressed, especially UV-stressed skin, and/or
- for treating mature skin and/or for slowing down skin aging The subject matter of the present invention also includes the use of a cosmetic composition comprising at least one compound from the group of AGEs for the non-therapeutic increase of energy metabolism, preferably for increase in the ATP synthesis rate in skin cells.

In the context of the present invention the term, "skin cells" is understood to mean all cells that are components of the human and/or animal skin itself, of the mucosa and the skin adnexa, in so far that they include living cells, in particular, hair follicles, hair roots, hair bulbs, the ventral epithelial layer of the nail bed (lectulus), as well as sebaceous glands and perspiratory glands.

The term, "skin cells" is also preferably understood to refer to organo-typical cell cultures as are described, for example, as reconstructed dermal papillae in European Patent No. 1 455 854 B1.

In the context of the present invention it was determined that a proliferation-inhibiting effect can be obtained by adding a composition comprising at least one compound from the group of the AGEs and/or their precursors (see Example 4). Substances that exert this type of effect are always wanted when the cell division is dysregulated. They can be employed, as non-limiting examples, in tumor therapy, against increased hair growth or thick hair, for deranged epidermal homeostasis or an excessive immune response.

By adding a composition comprising at least one compound from the group of AGEs and/or their precursors, the release of HGF (Hepatocyte Growth Factor) and KGF (Keratinocyte Growth Factor) in dermal papillae cells can be reduced (see Example 6).

Both growth factors HGF and KGF are important regulators of the hair cycle. Substances that induce a negative regulation of these factors are of great importance, should a reduction of hair growth and/or a reduction of hair thickness be desired.

Accordingly, a preferred embodiment of the invention is the use of a cosmetic composition comprising at least one compound from the group of the AGEs and/or their precursors for the therapeutic and non-therapeutic reduction of hair growth and/or for the reduction of hair thickness, preferably the cosmetic/non-therapeutic reduction of hair growth and/or reduction of hair thickness.

The subject matter of the present invention also includes use of a cosmetic composition comprising at least one compound from the group of AGEs for non-therapeutic inhibition of cell division activity of skin cells, preferably of fibroblasts.

In relation to the present invention, fibroblasts are understood to mean naturally occurring fibroblasts that occur principally in the dermis, genetically modified fibroblasts, or else fibroblasts or their precursors resulting from spontaneous mutation. The fibroblasts can be of animal or human origin.

The subject matter of the present invention is moreover the use of at least one compound from the group of the AGEs and/or their precursors for manufacturing a medicament for the inhibition of cell division activity of skin cells, preferably of fibroblasts.

In the context of the present invention it was moreover determined that compositions comprising at least one compound from the group of the AGEs and/or their precursors possess an anti-inflammatory effect and in particular reduce the basal release of the cytokine IL-8 (see Example 5).

Inflammation reactions of the skin can be of many types. Besides an incorrectly controlled regulation, such as is postulated in psoriasis or neurodermatitis, exogenic pollutants are frequently the causes for the development of typical characteristics of inflammation such as reddening, itching and pain. Central control molecules for these reactions are cytokines. These low molecular weight proteins are involved in the cascade of signals of the inflammation reactions. In this context the inflammation-promoting cytokine IL-8 with its diverse functions takes a central position. Substances that reduce the release of the IL-8 protein generally lead to a reduction of the inflammation reaction, thereby soothing the skin. Accordingly, a preferred embodiment of the invention is the use of a cosmetic composition comprising at least one compound from the group of the AGEs and/or their precursors for soothing the skin and/or for the non-therapeutic treatment of skin irritations, inflammation reactions of the skin and/or dry skin.

The subject matter of the present invention is also the use of a cosmetic composition comprising at least one compound from the group of the AGEs (advanced glycation end products) for the non-therapeutic inhibition of inflammation reactions of the skin, preferably for decreasing the basal release of the cytokine IL-8 in keratinocytes.

The subject matter of the present invention moreover includes use of at least one compound from the group of AGEs and/or their precursors for manufacturing a medicament for treatment of inflammation reactions of the skin, preferably for decreasing basal release of the cytokine IL-8 in keratinocytes.

In relation to the present invention, keratinocytes are understood to mean naturally occurring keratinocytes found principally in the epidermis, genetically modified keratinocytes or else keratinocytes or their precursors resulting from spontaneous mutation. The keratinocytes can be of animal or human origin.

In the context of the present invention, inflammation reactions are understood to include, as non-limiting examples, physiological processes such as dry skin, acne, skin irritations and/or pathological processes such as allergies, psoriasis, neurodermatitis or alopecia areata.

Due to the broad activity potential of AGEs and/or their precursors, use of the inventive compositions has a positive effect on skin. Sustainable skin protection and/or improved skin care is achieved due to increased energy metabolism, in particular the ATP synthesis rate, and inhibition of inflammation reactions and cell division activity.

At the same time further biological tests show that the inventive AGEs and/or their precursors do not generally have any side effects with respect to cell damage, preferably no effects with respect to membrane damage to the skin or skin cells, preferably to dermal papillae cells (see Example 2). In fact, experiments on cell vitality of the skin, preferably on cell vitality of cultivated fibroblasts, show that a cell activating effect results from use of compositions comprising at least one compound from the group of AGEs and/or their precursors. Cell damaging effects from the substances are generally not observed (see Example 1).

A further preferred embodiment includes use of an inventive cosmetic composition comprising at least one additional component chosen from emulsifiers or surfactants, cosmetic active ingredients, vitamins, protein hydrolyzates, film-forming substances, UV-filter substances, fragrances, conditioning agent active ingredients, thickeners, conservation agents, antioxidants, colorants, buffers, sequestrants, propellants, reducing agents, anti-dandruff active ingredients, tanning agents, moisturizers for the skin and/or lustering agents.

Emulsifiers act at the interface to produce water- or oil-stable adsorption layers that protect the dispersed droplets against coalescence, thereby stabilizing the emulsion. Thus, emulsifiers, like surfactants, are composed of hydrophobic and hydrophilic molecular moieties. Hydrophilic emulsifiers preferably form oil-in-water ('O/W') emulsions and hydrophobic emulsifiers preferably form water-in-oil ('W/O') emulsions. W/O emulsions that are stabilized in the absence of hydrophilic emulsifiers are disclosed in German Patent Application Publication Nos. DE 198 16 665 A1 and DE 198 01 593 A1. An emulsion is understood to mean a dispersion of a liquid in the form of droplets in another liquid using an energy input to afford interfaces stabilized with surfactants. Choice of this emulsifying surfactant or emulsifier depends on the materials being dispersed and the respective external phase, as well as the fineness of the emulsion.

Exemplary emulsifiers usable according to the invention include
- addition products of 4 to 30 moles ethylene oxide and/or 0 to 5 moles propylene oxide on linear $C_8$-$C_{22}$ fatty alcohols, on $C_{12}$-$C_{22}$ fatty acids and on $C_8$-$C_{15}$ alkylphenols;
- $C_{12}$-$C_{22}$ fatty acid mono and diesters of addition products of 1 to 30 moles ethylene oxide on $C_3$-$C_6$ polyols, particularly on glycerin;
- ethylene oxide and polyglycerine addition products on methyl glucoside fatty acid esters, fatty acid alkanolamides and fatty acid glucamides;
- $C_8$-$C_{22}$ alkyl mono and oligoglycosides and their ethoxylated analogs, wherein the preferred degrees of oligomerization are 1.1 to 5, particularly 1.2 to 2.0, and glucose is preferred as the sugar component;
- mixtures of alkyl (oligo) glucosides and fatty alcohols (e.g., the commercial product Montanov® 68 available from Seppic);
- addition products of 5 to 60 moles ethylene oxide on castor oil and hydrogenated castor oil;
- partial esters of polyols containing 3-6 carbon atoms with $C_8$-$C_{22}$ fatty acids;
- sterols (sterine). Sterols are understood to mean a group of steroids which carry a hydroxyl group on carbon atom 3 of the steroid skeleton and are isolated from both animal tissue (zoosterols) and vegetal fats (phytosterols). Examples of zoosterols include cholesterol and lanosterol. Examples of suitable phytosterols include beta-sitosterol, stigmasterol, campesterol and ergosterol. Sterols, the so-called mycosterols, are also isolated from fungi and yeasts.
- phospholipids, principally the glucose-phospholipids, which are obtained, for example, as lecithins or phosphatidyl cholines from, for example, egg yolk or plant seeds (e.g., soya beans);
- fatty acid esters of sugars and sugar alcohols such as sorbitol;
- polyglycerin and polyglycerin derivatives, preferably polyglyceryl-2-dipolyhydroxy stearate (commercial available as Dehymuls® PGPH from Cognis) and polyglyceryl-3-diisostearate (commercial available as Lameform® TGI from Cognis); and/or
- linear and branched $C_8$-$C_{30}$ fatty acids and their Na, K, ammonium, Ca, Mg and Zn salts.

The inventive compositions preferably comprise emulsifiers in quantities of 0.1 to 25 wt. %, particularly 0.5 to 15 wt. %, based on total weight of the composition.

In a particularly preferred embodiment, at least one non-ionic emulsifier with a HLB value of 8 and below is included (according to the definition of the HLB value shown in *Römpp-Lexikon Chemie*, Falbe and M. Regitz Eds., 10th Ed., Georg Thieme Verlag Stuttgart, New York, (1997), p. 1764). Exemplary suitable emulsifiers of this type are compounds of the general Formula $R^1$—O—$R^2$, wherein $R^1$ is a primary linear alkyl, alkenyl or acyl group having 20 to 30 carbon atoms and $R^2$ is hydrogen, a group of formula $((C_nH_{2n}O)_x$—H with x=1 or 2 and n=2 to 4 or a polyhydroxyalkyl group with 4 to 6 carbon atoms and 2 to 5 hydroxyl groups. A particularly preferred emulsifier of formula $R^1$—O—$R^2$ is a behenyl or erucyl derivative, wherein $R^1$ represents a primary linear alkyl, alkenyl or acyl group having 22 carbon atoms.

Further preferred suitable emulsifiers with a HLB value of 8 and below are the addition products of 1 or 2 moles ethylene oxide or propylene oxide on behenyl alcohol, erucyl alcohol, arachidyl alcohol or also on behenic acid or erucic acid. Monoesters of $C_{16}$-$C_{30}$ fatty acids with polyols such as pentaerythritol, trimethylol propane, diglycerin, sorbitol, glucose or methyl glucose are also suitable and preferred. Examples of such products include sorbitol monobehenate or pentaerythritol monoerucate.

In another similarly particularly preferred embodiment, at least one ionic emulsifier, selected from anionic, zwitterionic, ampholytic and cationic emulsifiers, is included. Preferred anionic surfactants include alkyl sulfates, alkyl polyglycol ether sulfates and ether carboxylic acids with 10 to 18 C atoms in the alkyl group and up to 12 glycol ether groups in the molecule, sulfosuccinic acid mono and dialkyl esters with 8 to 18 C atoms in the alkyl group and sulfosuccinic acid mono-alkylpolyoxyethyl esters with 8 to 18 C atoms in the alkyl group and 1 to 6 oxyethylene groups, monoglyceride sulfates, alkyl and alkenyl ether phosphates as well as condensates of protein and fatty acids. Zwitterionic emulsifiers carry at least a quaternary ammonium group and at least on —COO⁻ or —SO₃⁻ group in the molecule. Particularly suitable zwitterionic emulsifiers are the so-called betaines such as N-alkyl-N,N-dimethylammonium glycinates, N-acyl-aminopropyl-N,N-dimethylammonium glycinates and 2-alkyl-3-carboxymethyl-3-hydroxyethyl-imidazolines, each having 8 to 18 carbon atoms in the alkyl or acyl group, as well as cocoacylaminoethylhydroxyethylcarboxymethyl glycinate.

Ampholytic emulsifiers comprise, apart from a $C_{8-24}$ alkyl or acyl group, at least one free amino group and at least one —COOH or —SO₃H group in the molecule, and are able to form internal salts. Examples of suitable ampholytic emulsifiers are N-alkylglycines, N-alkylamino propionic acids, N-alkylamino butyric acids, N-alkylimino dipropionic acids, N-hydroxyethyl-N-alkylamido propylglycines, N-alkyltaurines, N-alkylsarcosines, 2-alkylamino propionic acids and alkylamino acetic acids, each with about 8 to 24 carbon atoms in the alkyl group.

Ionic emulsifiers can be included in quantities of 0.01 to 5 wt. %, preferably 0.05 to 3 wt. % and particularly preferably from 0.1 to 1 wt. %, based on total weight of the composition.

In addition, the inventive compositions may include foaming, non-ionic, zwitterionic, anionic and cationic surfactants.

Examples of non-ionic surfactants include—
alkoxylated fatty acid esters of the Formula $R^1CO$—$(OCH_2CHR^2)_xOR^3$, in which $R^1CO$-stands for a linear or branched, saturated and/or unsaturated acyl group with 6 to 22 carbon atoms, $R^2$ for hydrogen or methyl, $R^3$ for linear or branched alkyl groups with 1 to 4 carbon atoms and x for numbers from 1 to 20;
addition products of ethylene oxide to fatty acid alkanolamides and fatty amines;
fatty acid N-alkylglucamides;
$C_8$-$C_{22}$ alkylamine-N-oxides;
alkyl polyglycosides corresponding to the general formula RO—$(Z)_x$ wherein R stands for a $C_8$-$C_{16}$ alkyl, Z for sugar and x for the number of sugar units. The alkyl polyglycosides used according to the invention may simply comprise a defined alkyl group R. However, normally these compounds are manufactured from natural fats and oils or mineral oils. In such case, the alkyl groups R are present as mixtures corresponding to the starting compounds or to each of the compounds worked up. Alkyl polyglycosides are particularly preferred, wherein R is from $C_8$- and $C_{10}$-alkyl groups, from $C_{12}$ and $C_{14}$ alkyl groups, from $C_8$- to $C_{16}$ alkyl groups or from $C_{12}$- to $C_{16}$ alkyl groups.
Any mono or oligosaccharide can be employed as the sugar building block Z. Normally, sugars having 5 or 6 carbon atoms as well as the corresponding oligosaccharides are added (e.g., glucose, fructose, galactose, arabinose, ribose, xylose, lyxose, allose, altrose, mannose, gulose, idose, talose and sucrose). Preferred sugar building blocks include glucose, fructose, galactose, arabinose and sucrose, with glucose particularly preferred. The inventively usable alkyl polyglycosides comprise an average of 1.1 to 5, preferably 1.1 to 2.0, particularly preferably 1.1 to 1.8 sugar units. Alkoxylated homologs of the cited alkyl polyglycosides can also be used according to the invention. These homologs can comprise on average up to 10 ethylene oxide and/or propylene oxide units per alkyl glycoside unit.

Zwitterionic surfactants are designated as those surface-active compounds that carry at least one quaternary ammonium group and at least one —COO⁽⁻⁾ or —SO₃⁽⁻⁾ group in the molecule. Particularly suitable zwitterionic surfactants are the so-called betaines such as the N-alkyl-N,N-dimethylammonium glycinates, for example the cocoalkyldimethylammonium glycinate, N-acylaminopropyl-N,N-dimethylammonium glycinates, for example the cocoacylaminopropyldimethylammonium glycinate, and 2-alkyl-3-carboxymethyl-3-hydroxyethyl imidazolines with 8 to 18 carbon atoms in each of the alkyl or acyl groups, as well as cocoacylaminoethylhydroxyethylcarboxymethyl glycinate. A preferred zwitterionic surfactant is the fatty acid amide derivative known under the INCI name Cocamidopropyl Betaine.

Suitable anionic surfactants for the inventive preparations include all anionic surface-active materials that are suitable for use on the human body. They are characterized by a water solubilizing anionic group, such as a carboxylate, sulfate, sulfonate or phosphate group, and a lipophilic alkyl group containing about 8 to 30 carbon atoms. In addition, the molecule may comprise glycol or polyglycol ether groups, ester, ether and amide groups as well as hydroxyl groups. Exemplary suitable foaming anionic surfactants include—each in the form of sodium, potassium and ammonium as well as mono, di and trialkanolammonium salts with 2 to 4 carbon atoms in the alkanol group—
acylglutamates according to Formula (B-I)—

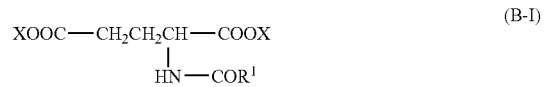

wherein $R^1CO$ represents a linear or branched acyl group with 6 to 22 carbon atoms and 0, 1, 2 or 3 double bonds, and X is hydrogen, an alkali and/or alkaline earth metal, ammonium, alkylammonium, alkanolammonium or glucammonium, for example, acylglutamates that derive from fatty acids having 6 to 22, preferably 12 to 18 carbon atoms, such as $C_{12/14}$- or $C_{12/18}$-cocofatty acid, lauric acid, myristic acid, palmitic acid and/or stearic acid, particularly sodium N-cocoyl- and sodium N-stearoyl-L-glutamate, esters of a hydroxy-substituted di or tricarboxylic acid according to the general Formula (B-II)—

wherein X is H or a —CH₂COOR group, Y is H or —OH, with the proviso that Y is H if X is —CH₂COOR; R, $R^1$ and $R^2$, independently of each other signify a hydrogen atom, an alkali or alkaline earth metal cation, an ammonium group, the cation of an ammonium organic base or a group Z which derives from a polyhydroxylated organic compound chosen from etherified $C_6$-$C_{18}$ alkylpolysaccharides having 1 to 6 monomeric saccharide units and/or etherified aliphatic $C_6$-$C_{16}$ hydroxyalkyl polyols having 2 to 16 hydroxyl groups, with the proviso that at least one of the groups R, $R^1$ and $R_2$ is a group Z;

esters of the sulfosuccinic acid of the general formula (B-III)—

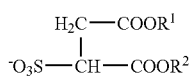
(B-III)

wherein $R^1$ and $R^2$, independently of one another represent a hydrogen atom, an alkali or alkaline earth metal cation, an ammonium group, the cation of an ammonium organic base or a group Z, which derives from a polyhydroxylated organic compound selected from the group of etherified $C_6$-$C_{18}$ alkylpolysaccharides having 1 to 6 monomeric saccharide units and/or the etherified aliphatic $C_6$-$C_{16}$ hydroxyalkyl polyols having 2 to 16 hydroxyl groups, with the proviso that at least one of the groups $R^1$ or $R^2$ is a group Z;

sulfosuccinic acid mono and dialkyl esters with 8 to 24 carbon atoms in the alkyl group and sulfosuccinic acid mono-alkylpolyoxyethyl esters with 8 to 24 C atoms in the alkyl group and 1 to 6 ethoxy groups;

esters of tartaric acid and citric acid with alcohols, which represent addition products of about 2-15 molecules of ethylene oxide and/or propylene oxide on fatty alcohols containing 8 to 22 carbon atoms;

linear and branched fatty acids with 8 to 30 carbon atoms (soaps);

ether carboxylic acids of the formula R—O—$(CH_2$—$CH_2O)_x$—$CH_2$—COOH, wherein R is a linear alkyl group with 8 to 30 carbon atoms and x=0 or 1 to 16;

acyl sarcosinates with a linear or branched acyl group having 6 to 22 carbon atoms and 0, 1, 2 or 3 double bonds;

acyl taurates with a linear or branched acyl group having 6 to 22 carbon atoms and 0, 1, 2 or 3 double bonds;

acyl isethionates with a linear or branched acyl group having 6 to 22 carbon atoms and 0, 1, 2 or 3 double bonds;

linear alkane sulfonates with 8 to 24 carbon atoms;

linear α-olefin sulfonates with 8 to 24 carbon atoms;

α-sulfo fatty acid methyl esters of fatty acids with 8 to 30 carbon atoms;

alkyl sulfates and alkyl polyglycol ether sulfates of the formula R—$O(CH_2$—$CH_2O)_x$—$SO_3X$, wherein R is preferably a linear alkyl group having 8 to 30 carbon atoms, particularly preferably 8 to 18 carbon atoms, z=0 or 1 to 12, particularly preferably 3, and X is a sodium, potassium, magnesium, zinc, ammonium ion or a monoalkanol-, dialkanol- or trialkanolammonium ion having 2 to 4 carbon atoms in the alkanol groups, wherein a particularly preferred example is zinc cocoyl ether sulfate having an ethoxylation degree of z=3;

mixtures of surface-active hydroxy sulfonates according to German Patent Application Publication No. DE 37 25 030 A;

sulfated hydroxyalkyl polyethylenes and/or hydroxyalkylene propylene glycol ethers according to German Patent Application Publication No. DE 37 23 354 A;

sulfonates of unsaturated fatty acids containing 8 to 24 carbon atoms and 1 to 6 double bonds according to German Patent Application Publication No. DE 39 26 344 A;

alkyl- and/or alkenyl ether phosphates of Formula (B-IV)—

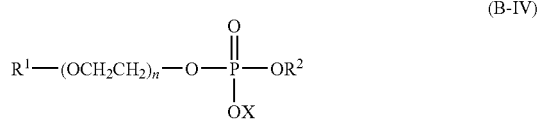
(B-IV)

wherein $R^1$ preferably represents an aliphatic hydrocarbon group with 8 to 30 carbon atoms, $R^2$ represents hydrogen, a $(CH_2CH_2O)_n R^1$ group or X, n for numbers between 1 and 10 and X for hydrogen, an alkali or alkaline earth metal or $NR^3R^4R^5R^6$, with $R^3$ to $R^6$, independently of each other standing for a $C_1$ to $C_4$ hydrocarbon group;

sulfated fatty acid alkylene glycol esters of the formula $RCO(AlkO)_n SO_3 M$, wherein RCO— represents a linear or branched, aliphatic, saturated and/or unsaturated acyl group with 6 to 22 carbon atoms, Alk represents $CH_2CH_2$, $CHCH_3CH_2$ and/or $CH_2CHCH_3$, n represents numbers from 0.5 to 5 and M represents a cation, such as described in German Patent Application No. DE 197 36 906.5;

monoglyceride sulfates and monoglyceride ether sulfates according to Formula (B-V)—

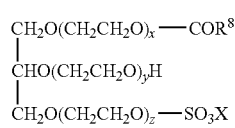
(B-V)

wherein $R^8CO$ stands for a linear or branched acyl group with 6 to 22 carbon atoms, the sum of x, y and z is 0 or stands for numbers from 1 to 30, preferably 2 to 10, and X stands for an alkali metal or alkaline earth metal. In the context of the invention, typical examples of suitable monoglyceride (ether) sulfates include the reaction products of lauric acid monoglyceride, cocoa fatty acid monoglyceride, palmitic acid monoglyceride, stearic acid monoglyceride, oleic acid monoglyceride and tallow fatty acid monoglyceride as well as their ethylene oxide adducts with sulfur trioxide or chlorosulfonic acid in the form of their sodium salts. Preferably, monoglyceride sulfates of Formula (VI) are added, in which $R^8CO$ stands for a linear acyl group with 8 to 18 carbon atoms.

The cosmetic active substance present in a fraction of 0.0001-38 wt. %, based on total weight of the composition, is preferably chosen from the following products or their mixtures:

anti-perspirants,
deodorants,
monomers, oligomers and/or polymers of amino acids, N—$C_2$-$C_{24}$ acylamino acids, the esters and/or the physiologically compatible salts of these substances,
DNA- or RNA-oligonucleotides,
natural betaine compounds,
α-hydroxycarboxylic acids, α-ketocarboxylic acids, β-hydroxycarboxylic acids and their esters, lactones or salts,
flavonoids and flavonoid-rich plant extracts,
isoflavonoids and isoflavonoid-rich plant extracts,
polyphenols and polyphenol-rich plant extracts,
ubiquinone and ubiquinol as well as their derivatives,
silymarine,
ectoine,
repellents, self-tanning active substances,
skin-lightening active substances,
skin-soothing active substances,
moisture-donating active substances, and/or
sebum-regulating active substances, In a preferred embodiment, compositions according to the invention comprise at least one vitamin, provitamin, or a compound designated as a vitamin precursor, from the vitamin groups A, B, C, E, H, and K and the esters of the aforementioned substances.

Retinol (vitamin $A_1$), as well as 3,4-didehydroretinol, (vitamin $A_2$), belong in the group of substances designated as vitamin A. β-carotene is the provitamin of retinol. Examples of vitamin A components according to the invention include vitamin A acid and its esters, vitamin A aldehyde and vitamin A alcohol as well as its esters, such as retinyl palmitate and retinyl acetate. Compositions according to the invention preferably comprise vitamin A components in amounts of 0.05 to 1 wt. %, based on total weight of the composition.

The vitamin B group or the vitamin B complex include, inter alia— vitamin $B_1$, trivial name thiamine, chemical name 3-[(4'-amino-2'-methyl-5'-pyrimidinyl)-methyl]-5-(2-hydroxyethyl)-4-methylthiazolium chloride. Thiamine hydrochloride is preferably added in amounts of 0.05 to 1 wt %, based on total weight of the composition.

vitamin $B_2$, also known as riboflavin (chemical name 7,8-dimethyl-10-(1-D-ribityl)-benzo[g]pteridine-2,4(3H,10H)-dione). Riboflavin or its derivatives are preferably added in amounts of 0.05 to 1 wt. %, based on the total composition.

vitamin $B_3$. The compounds Nicotinic acid and Nicotinamide (Niacinamide) are included under this designation. According to the invention, Nicotinamide is preferred and is found in compositions according to the invention in amounts of 0.05 to 1 wt. %, based on total weight of the composition.

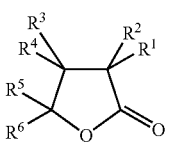

(B-VI)

vitamin $B_6$, understood not to mean a pure substance, but rather the known derivatives of 5-hydroxymethyl-2-methylpyridin-3-ol with the trivial names pyridoxine, pyridoxamine and pyridoxal. Compositions according to the invention preferably comprise Vitamin $B_6$ in amounts of 0.0001 to 1.0 wt. %, particularly in amounts of 0.001 to 0.01 wt. %, based on total weight of the composition.

vitamin $B_7$ (biotin), also designated as Vitamin H or "skin vitamin". Biotin is (3aS,4S,6aR)-2-oxohexahydrothienol[3,4-d]-imidazol-4-valeric acid. The compositions according to the invention preferably comprise biotin in amounts of 0.0001 to 1.0 wt. %, particularly in amounts of 0.001 to 0.01 wt. %, based on total weight of the composition.

Vitamin C (ascorbic acid) is preferably added in amounts of 0.1 to 3 wt. %, based on total weight of the composition. Use of the derivatives ascorbyl palmitate, -stearate, -dipalmitate, -acetate, Mg ascorbyl phosphate, Na ascorbyl phosphate, sodium and magnesium ascorbate, disodium ascorbyl phosphate and -sulfate, potassium ascorbyl tocopheryl phosphate, chitosan ascorbate or ascorbyl glucoside can be preferred. Use in combination with tocopherols can also be preferred.

The vitamin E group includes tocopherol, in particular α-tocopherol, and its derivatives. Preferred derivatives include in particular the esters, such as tocopheryl acetate, tocopheryl nicotinate, tocopheryl phosphate, tocopheryl succinate, tocopheryl linoleate, tocopheryl oleate, tocophereth-5, tocophereth-10, tocophereth-12, tocophereth-18, tocophereth-50, and tocophersolan. Tocopherol and its derivatives are comprised in amounts of 0.05 to 1 wt. %, based on total weight of the composition. The term "vitamin F" usually refers to essential fatty acids, particularly linoleic acid, linolenic acid and arachidonoic acid.

Vitamin H is another term for biotin or vitamin $B_7$ (see above).

Among the fat-soluble vitamins of the vitamin K group, based on the fundamental structure of 2-methyl-1,4-naphthoquinone, are phylloquinone (vitamin $K_1$), farnoquinone or menaquinone-7 (vitamin $K_2$) and menadione (vitamin $K_3$). Vitamin K is preferably comprised in amounts of 0.0001 wt. % to 1.0 wt. %, particularly 0.01 wt. % to 0.5 wt. %, each based on total weight of the composition.

Vitamin A palmitate (retinyl palmitate), panthenol, nicotinic acid amide, pyridoxine, pyridoxamine, pyridoxal, biotin, ascorbyl palmitate and acetate, Mg ascorbyl phosphate, Na ascorbyl phosphate, sodium and magnesium ascorbate and the tocopherol esters, especially tocopheryl acetate, are particularly preferred according to the invention.

A preferred cosmetic composition is in the form of a balm, tablet, lotion, cream, emulsion, milk, paste, gel, foam or spray, particularly in emulsified form.

Use of an inventive cosmetic composition in the form of a shampoo, hair conditioner, hair gel, hair water, hair cure, hair cream, hair lotion, hair spray and hair tincture is preferred.

EXAMPLES a) Synthesis of AGEs by Treating Sugars with Amino Acids

General Working Protocol AAV1:

Sugar (40 mmol) and an amino acid (8 to 10 mmol) were added to a buffer solution (pH 7.0), and the reaction mixture was stirred at the relevant temperature for four hours in a three-necked flask equipped with a reflux condenser. Half of the solvent was removed in a rotary evaporator, and the product was then isolated by freeze-drying. The presence of any unreacted amino acid could not be detected in any isolated product.

A-1 Reaction of L-Lysine with Lactose (1:5)

Starting Materials:

| | |
|---|---|
| D-(+)-lactose | m = 13.7 g M = 342.3 g/mol |
| CAS: 200-559-2; Riedel de Haen, monohydrate (dried over silica gel at 70° C. in a vacuum oven) | (40 mmol) |
| L-lysine | m = 1.17 g |
| S-2-6-diamino caproic acid | (8 mmol) |
| M = 146.2 g/mol | |
| CAS: 56-87-1, Fluka ≧ 98% | |

Buffer solution pH 7.0
  200 mL phosphate mixture, B. Kraft GmbH
Experimental Procedure:
  According to general working protocol AAV1, stirred 4 hr at 95° C.
Results:
  m (crude product)=15.45 g (voluminous lyophilisate, brown)

A-2 Reaction of L-Lysine with Lactose (1:5)
Starting Materials:

| | |
|---|---|
| D-(+)-geleslactose | m = 14.4 g |
| M = 360.31 g/mol | (40 mmol) |
| CAS: 200-559-2; Riedel de Haen, monohydrate | |
| L-lysine | m = 1.17 g |
| S-2-6-diamino caproic acid | (8 mmol) |
| M = 146.2 g/mol | |
| CAS: 56-87-1, Fluka ≧ 98% | |
| Buffer solution pH 7.0 | 200 mL |
| phosphate mixture, B. Kraft GmbH | |

Experimental Procedure:
  According to general working protocol AAV1, stirred 4 hr at 60° C.
Results:
  m (crude product)=16.24 g (voluminous lyophilisate, light yellow)

A-3 Reaction of L-Lysine with Lactose (1:5)
Starting Materials:

| | |
|---|---|
| D-(+)-lactose | m = 14.4 g |
| M = 360.31 g/mol | (40 mmol) |
| CAS: 200-559-2; Riedel de Haen, monohydrate | |
| L-lysine | m = 1.17 g |
| S-2-6-diamino caproic acid | (8 mmol) |
| M = 146.2 g/mol | |
| CAS: 56-87-1, Fluka ≧ 98% | |
| Buffer solution pH 7.0 | 200 mL |
| phosphate mixture, B. Kraft GmbH | |

Experimental Procedure:
  According to general working protocol AAV1, stirred 4 hr at 35° C.
Results:
  m (crude product)=14.88 g (voluminous lyophilisate, light yellow)

A-4 Reaction of L-Arginine with Glucose (1:4)
Starting Materials:

| | |
|---|---|
| D-(+)-glucose | m = 7.21 g |
| M = 180.16 g/mol | (40 mmol) |
| CAS: 492-62-6, Fluka ≧ 99% | |
| L-arginine | m = 1.74 g |
| S-2-amino-5-guanidino-valeric acid | (10 mmol) |
| M = 174.2 g/mol | |
| CAS: 74-79-3, Fluka ≧ 99% | |
| Buffer solution pH 7.0 | 200 mL |
| phosphate mixture, B. Kraft GmbH | |

Experimental Procedure:
  According to general working protocol AAV1, stirred 4 hr at 95° C.
Results:
  m (crude product)=10.01 g (voluminous lyophilisate, brown)

A-5 Reaction of L-Arginine with Glucose (1:4)
Starting Materials:

| | |
|---|---|
| D-(+)-glucose | m = 7.21 g |
| M = 180.16 g/mol | (40 mmol) |
| CAS: 492-62-6, Fluka ≧ 99% | |
| L-arginine | m = 1.74 g |
| S-2-amino-5-guanidino-valeric acid | (10 mmol) |
| M = 174.2 g/mol | |
| CAS: 74-79-3, Fluka ≧ 99% | |
| Buffer solution pH 7.0 | 200 mL |
| phosphate mixture, B. Kraft GmbH | |

Experimental Procedure:
  According to general working protocol AAV1, stirred 4 hr at 60° C.
Results:
  m (crude product)=8.52 g (voluminous lyophilisate, light yellow)

A-6 Reaction of L-Arginine with Glucose (1:4)
Starting Materials:

| | |
|---|---|
| D-(+)-glucose | m = 7.21 g |
| M = 180.16 g/mol | (40 mmol) |
| CAS: 492-62-6, Fluka ≧ 99% | |
| L-arginine | m = 1.74 g |
| S-2-amino-5-guanidino-valeric acid | (10 mmol) |
| M = 174.2 g/mol | |
| CAS: 74-79-3, Fluka ≧ 99% | |
| Buffer solution pH 7.0 | 200 mL |
| phosphate mixture, B. Kraft GmbH | |

Experimental Procedure:
  According to general working protocol AAV1, stirred 4 hr at 35° C.
Results:
  m (crude product)=9.71 g (voluminous lyophilisate, light yellow)

b) Biological Tests

Example 1

Determination of the Cell Activity of Cultivated Fibroblasts after Treatment with Substances A-1, A-2, A-3, A-4, A-5 and A-6

Vitality of the cultivated cells was determined by means of redox dyes. These dyes penetrate into the cells and are reduced by electron capture at the external mitochondrial membrane. This reduction requires a color change that is subsequently photometrically analyzed.

Vitality was quantified by setting the untreated control to 100% and the measured values of the samples treated with the substances were in reference to that figure. Cell damaging means a relative vitality of less than 80%, and cell activating means greater than or equal to 120%.

Cell Proliferation Reagent Wst-1 (Roche Applied Science, Mannheim, Germany) was used for this test.

TABLE 1

Relative vitality after treating fibroblasts with substances A-1, A-2, A-3, A-4, A-5 and A-6

| Substance | Concentration µg/ml | Vitality MW | SD |
|---|---|---|---|
| Glucose | 0 | 100 | |
| | 250 | 111.6 | 5.8 |
| | 500 | 96.1 | 12.0 |
| | 1000 | 103.1 | 7.3 |
| | 2000 | 105.2 | 5.9 |
| | 4000 | 144.2 | 8.6 |
| Lactose | 0 | 100.0 | |
| | 250 | 97.5 | 7.4 |
| | 500 | 98.6 | 3.3 |
| | 1000 | 102.0 | 5.7 |
| | 2000 | 116.4 | 3.9 |
| | 4000 | 119.8 | 4.0 |
| A-1 | 0 | 100.0 | |
| | 63 | 104.4 | 11.2 |
| | 125 | 117.2 | 20.3 |
| | 250 | 140.2 | 24.9 |
| | 500 | 142.0 | 19.5 |
| | 1000 | 204.1 | 32.8 |
| A-2 | 0 | 100.0 | |
| | 63 | 99.9 | 7.9 |
| | 125 | 97.3 | 9.6 |
| | 250 | 104.9 | 10.7 |
| | 500 | 132.8 | 14.3 |
| | 1000 | 175.7 | 12.7 |
| A-3 | 0 | 100.0 | |
| | 63 | 110.3 | 11.2 |
| | 125 | 111.2 | 10.0 |
| | 250 | 108.2 | 11.1 |
| | 500 | 114.4 | 9.0 |
| | 1000 | 163.7 | 23.2 |
| A-4 | 0 | 100.0 | |
| | 63 | 118.2 | 3.8 |
| | 125 | 113.9 | 7.0 |
| | 250 | 113.9 | 7.5 |
| | 500 | 127.0 | 9.1 |
| | 1000 | 131.9 | 12.6 |
| A-5 | 0 | 100.0 | |
| | 63 | 102.5 | 9.7 |
| | 125 | 104.0 | 6.9 |
| | 250 | 116.1 | 10.4 |
| | 500 | 139.3 | 12.7 |
| | 1000 | 148.4 | 16.1 |
| A-6 | 0 | 100.0 | |
| | 63 | 116.4 | 10.8 |
| | 125 | 117.3 | 5.2 |
| | 250 | 114.9 | 4.3 |
| | 500 | 147.3 | 2.9 |
| | 1000 | 157.3 | 8.5 |

MW (mean value),
SD (standard deviation).

All added substances had a concentration-dependent effect on the vitality of the studied fibroblasts. In particular A1, A-2 and A3 significantly promote the cell activity. Within these tests, an effect due to the sugar monomers could be excluded.

Example 2

Determination of Cell-Damaging Side Effects from Treatment with Substances A-1, A-2, A-3, A-4, A-5 and A-6

Determination of the release of lactate dehydrogenase (LDH) cultivated cells provides information on the damage of the cell membrane. In undamaged cells, LDH is localized exclusively in the cytoplasma. LDH can only diffuse into the surrounding culture medium once the cell membrane has been damaged. The quantity of released LDH can be determined by means of a substrate-coupled colorimetric test system.

In order to determine possible cell-damaging side effects, reconstructed dermal papillae in accordance with European Patent No. 1 455 854 were cultivated with the test substances, and after treatment the quantity of LDH was analyzed in the medium.

Time required for a color change of a defined quantity of dye was measured for Table 2. Here values>100% mean no cell-damaging effects, whereas values<80% point to possible cell-damaging reactions.

The Cytotoxicity Detection Kit available from Roche (Mannheim, Germany) was used for this test following the guidelines of the manufacturer.

TABLE 2

Analysis of release of lactate dehydrogenase after treatment with substances

| Substance | Added concentration w/v[a] | Cytotoxicity (% rel to control) | CV %[b] |
|---|---|---|---|
| A-1 | 0.01% | 95.7 | 12.6 |
| | 0.10% | 105.9 | 18.8 |
| | 0.50% | 107.4 | 6.1 |
| A-2 | 0.01% | 100.0 | 1.6 |
| | 0.10% | 103.1 | 2.1 |
| | 0.50% | 92.2 | 14.9 |
| A-3 | 0.01% | 99.2 | 5.5 |
| | 0.10% | 104.8 | 3.0 |
| | 0.50% | 101.9 | 1.0 |
| A-4 | 0.01% | 105.7 | 4.0 |
| | 0.10% | 102.9 | 6.0 |
| | 0.50% | 93.9 | 5.7 |
| A-5 | 0.01% | 95.9 | 5.0 |
| | 0.10% | 100.5 | 2.0 |
| | 0.50% | 94.9 | 7.6 |
| A-6 | 0.01% | 92.2 | 10.6 |
| | 0.10% | 98.8 | 1.2 |
| | 0.50% | 75.6 | 2.0 |

[a]Weight per volume (w/v) in %
[b]Variability coefficient; standard deviation from the arithmetic mean t Compared with the untreated controls, a cell-damaging effect could be detected only for substance A-6 at the highest concentration (0.5%).

Example 3

Detection of ATP-Synthesis Rate for Substances A-1, A-2 and A-4

ATP (adenosine triphosphate) is the universal storage form for chemical energy in cells. ADP and $P_i$ (inorganic phosphate) are formed by cleavage of the distal phosphate group. This reaction is strongly exergonic (i.e., energy releasing). ATP is produced by the cellular, oxidative decomposition of fats, carbohydrates and proteins. It acts as an energy supplier for biochemical syntheses, for transport processes (active transport) and for mechanical work. These processes are endergonic (i.e., they only occur under energy input). In order to optimally sustain their metabolism, cells are therefore reliant on an adequate supply of ATP. For example, dermal papillae cells also need ATP for the production of growth factors and therewith the control of the hair cycle. The proliferation and differentiation of hair shaft keratinocytes is likewise coupled to ATP synthesis as the biosynthesis of specific proteins is an essential requirement for both processes. If the ATP synthesis rate of cells relevant to hair can be increased, then more energy is available to the cells in order to sustain metabolic processes and cellular structures, and in order to renew structures (e.g., for repair processes or the new growth of hair).

ATP Detection Methods—

ATP determinations were made using the ATPLite™-M Assays (from Packard). The test principle of this assay is based on the fact that the lucerifase from *Photinus pyralis* catalyzes a reaction in which, in the presence of ATP, D-luciferin is converted to oxyluciferin. Green light is emitted in this reaction and can be measured with an illuminometer. The emitted bioluminescence light is proportional to the amount of ATP present.

Determination of ATP activity is carried out in organo-typical cell cultures (reconstructed dermal papillae according to EP 1 455 854). Treatment with the substance mixture is carried out for 24 hours against an untreated control. The cells were then lysed with 100 μl/cavity of a lyse buffer contained in a test kit for 5 minutes on a shaker. The cells were then incubated an additional 5 minutes with 100 μl/cavity of the supplied substrate solution on the shaker, and the reaction mixture was subsequently transferred into a black microtitre plate. Luminescence was measured after an incubation time of 10 minutes in the dark.

TABLE 3

Effect of A-1, A-2 and A-4 on ATP production of organo-typical cell cultures in %

| Substance | Conc.[a] | 3 h Mean[b] | SD[c] | 6 h Mean | SD | 24 h Mean | SD |
|---|---|---|---|---|---|---|---|
| A-1 | 0.05 | 144 | 17.2 | 100 | 21.7 | 74 | 3.5 |
|  | 0.01 | 145 | 11.6 | 109 | 7.5 | 103 | 7.7 |
| A-2 | 0.10 | 122 | 9.4 | 104 | 12.4 | 94 | 3.4 |
|  | 0.05 | 112 | 17.2 | 106 | 4.8 | 91 | 7.8 |
|  | 0.01 | 139 | 15.2 | 104 | 13.6 | 94 | 8.6 |
| A-4 | 0.05 | 143 | 22.9 | 105 | 2.1 | 85 | 11.7 |
|  | 0.01 | 128 | 8.4 | 100 | 10.8 | 96 | 6.6 |

[a]Weight per volume (w/v) in %
[b]Arithmetic mean;
[c]Standard deviation

All three investigated substances promote at an early stage the increased synthesis of ATP in dermal papillae cells and supports thereby synthetic performance of the skin, in particular, ATP synthesis on the hair root.

Analysis of the pure glucose and lactose did not lead at any time and at any concentration to a change in the synthesis rate of ATP.

Example 4

Determination of Proliferation of Fibroblasts after Treatment with Substances A-4, A-5 and A-6

Determination of the proliferation of the cultivated cells provides information on the status of the cell division of the treated cells. Both cell division stimulating and cell division inhibiting substances can be defined with this analysis. An outstanding feature during the cell division is the duplication of the DNA. During the new synthesis, nucleotides are built into the newly formed DNA strand. The proliferation can be measured by offering a non-natural nucleotide derivative (bromo deoxy uridine, BrdU) to the cells for the new synthesis; the BrdU can be subsequently detected with specific antibodies. The amount of newly synthesized DNA can be quantified fluorimetrically and provides proportional information on the degree of the cell division process.

Proliferation was determined by setting the untreated control to 100% and the measured values of the samples treated with the substances were in reference to that figure. For a relative proliferation of less than 80% the substance effect is said to be inhibitive, for greater than or equal to 120% the substance effect is considered to be stimulative.

The CyQuant Assay Cell Proliferation Assay from Molecular Probes was used for this test according to manufacturer's directions.

TABLE 4

Determination of Proliferation by Cyquant. Results after treatment of fibroblasts with A-4, A-5 and A-6.

| Substance | Concentration μg/ml | Proliferation MW | SD |
|---|---|---|---|
| Glucose | 0 | 100 |  |
|  | 250 | 79.6 | 21.2 |
|  | 500 | 71.8 | 23.3 |
|  | 1000 | 118.9 | 23.9 |
|  | 2000 | 90.5 | 13.4 |
|  | 4000 | 122.2 | 8.4 |
| Lactose | 0 | 100.0 |  |
|  | 250 | 107.2 | 22.8 |
|  | 500 | 90.4 | 23.1 |
|  | 1000 | 111.7 | 9.3 |
|  | 2000 | 107.6 | 12.0 |
|  | 4000 | 77.5 | 27.5 |
| A-4 | 0 | 100.0 |  |
|  | 63 | 54.6 | 10.1 |
|  | 125 | 51.9 | 10.3 |
|  | 250 | 63.3 | 10.1 |
|  | 500 | 47.2 | 7.3 |
|  | 1000 | 66.2 | 7.8 |
| A-5 | 0 | 100.0 |  |
|  | 63 | 57.7 | 21.1 |
|  | 125 | 64.8 | 6.6 |
|  | 250 | 101.2 | 18.8 |
|  | 500 | 103.2 | 9.4 |
|  | 1000 | 119.4 | 26.1 |
| A-6 | 0 | 100.0 |  |
|  | 63 | 45.1 | 12.0 |
|  | 125 | 63.4 | 17.1 |
|  | 250 | 59.5 | 15.1 |
|  | 500 | 73.4 | 12.1 |
|  | 1000 | 82.9 | 20.8 |

A significant decrease in the cell division activity on fibroblasts could be obtained by the concentration-dependent treatment with the substances A-4, A-5 and A-6. No effect could be detected for the sugar moieties (glucose, lactose).

Proliferation-inhibiting effects are always wanted when the cell division is dysregulated. Consequently, the inventive substances could be employed for example against increased hair growth or thick hair.

Example 5

Determination of the Release of IL-8 from HaCaT Keratinocytes after Treatment with A-2, A-3, A-5 and A-6

Measurement of the basal release of IL-8 provides information on the effects of substances on inflammation reactions. IL-8 is a pro-inflammatory cytokine, which plays a central role in the inflammation cascade of the skin. A reduction of the basal release of IL-8 points to potential inflammation inhibiting effects of the studied substances.

In order to determine the release of the IL-8, HaCaT keratinocytes were incubated in Hanks medium with glutamax, 5% FCS and antibiotics in 24 well culture vessels. On day 2 after seeding, cells were incubated with the test substances in a concentration of 0.5%. After treatment for 15-20 h the cell culture supernatant was removed and the amount of released IL-8 was quantified by ELISA.

The Quantikine IL-8 from RnD-Systems (Wiesbaden, Germany) was used for these analyses.

Values illustrated in Table 5 are relative values with respect to the untreated controls from 4 independent experiments.

TABLE 5

Relative basal release of IL-8 with respect to untreated controls after treatment of HaCaT keratinocytes with A-2, A-3, A-5 and A-6 at an added concentration of 0.5%. The mean values (MW) of four independent experiments, the corresponding standard deviations (SD) and significances by the T-test are given.

|        | Control | A-2    | A-3    | A-5    | A-6    |
|--------|---------|--------|--------|--------|--------|
| MW     | 100.00  | 75.4   | 83.9   | 65.8   | 59.9   |
| SD     | 0       | 11.8   | 12.3   | 12.7   | 20.8   |
| T-Test |         | 0.0060 | 0.0392 | 0.0017 | 0.0083 |

All substances lead to a significant reduction of the basal release of IL-8. Tests of glucose and lactose, each in a concentration of 0.5%, did not lead to a significant change in the basal release of IL-8 in any experiment. On the basis of these results it can be assumed that the substances A-2 and A-3 have an inflammation-inhibiting effect and the substances A-5 and A-6 have a special inflammation-inhibiting effect.

Example 6

Determination of Release of Growth Factors

Both the Hepatocyte Growth Factor (HGF) and Keratinocyte Growth Factor (KGF) are important regulators of the hair cycle. A change in the availability for the substances that regulate the hair cycle in comparison with the untreated controls should be assumed. The release of HGF and KGF can be quantified with the help of commercially available ELISA kits (Quantikine, RnD-Systems, Wiesbaden, Germany). For this, reconstructed hair follicle models, which are described in the European patent 1 455 854, were incubated with the test substances for 72 hours and the concentration of the growth factors in the medium was determined in the described manner. In order to be able to rule out that the described effects could have been caused by unreacted sugar (glucose or lactose), the respective individual components were tested at the highest possible concentration. The quantities of the untreated controls were set to 100% and the quantities of the treated samples were relative to these. The standard deviations were calculated from the three biological approaches.

TABLE 6

Analysis of KGF and HGF release in [%] after treatment of reconstructed hair follicle in comparison with untreated controls

| Substance | Added conc.[a] | HGF MW % | HGF SD % | KGF MW % | KGF SD % |
|-----------|----------------|----------|----------|----------|----------|
| Untreated | 0%             | 100.0    | 25.0     | 100.0    | 20.5     |
| A-1       | 0.01%          | 90.6     | 17.1     | 80.7     | 2.6      |
|           | 0.05%          | 83.7     | 18.8     | 80.6     | 21.2     |
|           | 0.10%          | 72.7     | 2.8      | 75.8     | 13.0     |
|           | 0.50%          | 68.1     | 7.2      | 58.0     | 2.2      |
| A-2       | 0.01%          | 90.2     | 8.2      | 85.3     | 7.1      |
|           | 0.05%          | 114.3    | 25.5     | 126.6    | 10.8     |
|           | 0.10%          | 76.2     | 6.9      | 102.7    | 20.0     |
|           | 0.50%          | 78.4     | 23.0     | 111.2    | 30.0     |
| A-3       | 0.01%          | 68.4     | 14.6     | 94.8     | 14.1     |
|           | 0.10%          | 59.6     | 17.5     | 81.0     | 16.1     |
|           | 0.50%          | 56.3     | 18.2     | 83.7     | 12.5     |

TABLE 6-continued

Analysis of KGF and HGF release in [%] after treatment of reconstructed hair follicle in comparison with untreated controls

| Substance | Added conc.[a] | HGF MW % | HGF SD % | KGF MW % | KGF SD % |
|-----------|----------------|----------|----------|----------|----------|
| A-4       | 0.01%          | 92.0     | 20.3     | 87.4     | 12.5     |
|           | 0.05%          | 84.6     | 19.8     | 104.2    | 31.1     |
|           | 0.10%          | 63.0     | 12.8     | 78.9     | 20.4     |
|           | 0.50%          | 55.0     | 2.4      | 62.3     | 6.5      |
| A-5       | 0.01%          | 60.6     | 0.5      | 92.3     | 14.1     |
|           | 0.10%          | 63.9     | 10.2     | 90.5     | 22.0     |
|           | 0.50%          | 66.4     | 4.6      | 77.7     | 6.4      |
| A-6       | 0.01%          | 66.2     | 8.4      | 102.4    | 22.8     |
|           | 0.10%          | 69.0     | 24.1     | 68.6     | 17.9     |
|           | 0.50%          | 79.0     | 27.8     | 93.4     | 29.0     |
| Lactose   | 0.40%          | 65.3     | 8.0      | 101.2    | 12.8     |
| Glucose   | 0.40%          | 87.6     | 7.2      | 88.6     | 13.2     |
| Untreated | 0%             | 100      | 8        | 100      | 14       |

[a]Weight per volume (w/v) in %

Based on the release of HGF after treatment of the reconstructed hair follicle model, it can be recorded that all test substances lead in a corresponding degree to a negative regulation. Particularly prominent and concentration-dependent effects were recorded for A-1, A-3 and A-4. Treatment with pure lactose and to a lesser extent also glucose likewise leads to a reduced release of HGF.

In regard to the KGF release, a reduced release was likewise recorded for the tested substances. It was particularly noticeable here that the hair follicle models react to the substance A-1. A distinct effect due to treatment with sugars (lactose and glucose) could not be established.

Based on the available data, the abovementioned substances induce distinct effects.

Both of the growth factors are important messengers for regulation of the hair cycle. HGF and KGF are produced and released by dermal papillae cells of the hair follicle, principally in order to control processes in the (anagen) growth phase, such as cell division activity of the hair keratinocytes. If, as described for some substances, the release of these growth factors is reduced, then it can lead to a potential halt of the growth phase. This means that the hair no longer grows, crossing over into the regression phase of the hair cycle, and falls out.

Based on this, the tested substances have the potential as an anti-hair growth active principle.

Example 7

The effect of AGEs on the gene expression profile of dermal papillae cells was tested.

Reconstructed dermal papillae as described in European patent 1 455 854 were systemically treated for 24 hours with each of the test substances listed in Table 7 in the cited concentrations. The relative gene expression profile was determined for the markers HGF and KGF (important markers of the anagen phase of the hair cycle) and TGF-beta 1, TGF-beta 2 and IGFBP3 (important markers of the catagen phase of the hair cycle). Expression for incubation with the untreated medium served as the reference; values presented in the Table illustrate the differential gene expression. A differential gene expression that is 1.66 times or greater than the absolute numerical value of the control gene expression is regarded as significant.

TABLE 7

Study of the relative gene expression profile of the relevant marker of the hair cycle for incubation with various AGEs and/or their precursors; addition concentrations in wt. %; the numbers in brackets following the substance names refer to the above listed structural formulas.

| Substances | Conc. | Anagen | | Catagen | | |
|---|---|---|---|---|---|---|
| | | HGF | KGF | TGFβ1 | TGFβ2 | IGFBP3 |
| untreated/only medium | | 1.00 | 1.00 | 1.00 | 1.00 | 1.00 |
| Maltol | 0.025% | 1.07 | −3.02 | −1.20 | −3.21 | −3.63 |
| Maltol | 0.01% | −1.23 | −1.87 | −1.28 | −1.86 | −1.69 |
| Fructoselysine (12) | 0.1% | −1.69 | −2.49 | −1.10 | −2.40 | −1.83 |
| Fructoselysine | 0.01% | −1.92 | −1.96 | 1.04 | −2.40 | −1.44 |
| 3-Desoxyglucosulose (18) | 0.1% | −1.78 | −1.93 | −1.27 | −1.54 | −2.12 |
| 3-Desoxyglucosulose | 0.01% | −2.09 | −1.33 | 1.02 | −1.67 | −1.20 |
| Ornithinoimidazolinone (16) | 0.1% | −3.30 | −1.25 | 1.08 | −1.66 | −1.60 |
| Maltosine (15) | 0.1% | −2.09 | −1.45 | 3.39 | −2.24 | 7.55 |
| Carboxymethyllysine (13) | 0.1% | −1.77 | 1.24 | 1.35 | −1.07 | 1.98 |

Reduction of the gene expression of markers of anagen, and thereby a reduced release of the growth factor as already discussed in Example 6, is a significant indication of the aptitude of the tested substances (in Table 7) for use as anti-hair growth agents (especially for cosmetic or non-therapeutic use).

Similarly, a simultaneously increased gene expression of markers of catagen is particularly observed for 0.1 wt. % maltosine. TGF-beta 1 induces apoptose (the programmed cell death) in keratinocytes, thereby terminating elongation of the hair shaft and thus hair growth. Maltosine appears to be particularly suitable for use as an anti-hair growth agent (in particular, in the context of a cosmetic or non-therapeutic use).

Although the present invention has been described in detail, it is to be clearly understood that the same is by way of illustration and example only, and is not to be taken as a limitation. The spirit and scope of the present invention are to be limited only by the terms of any claims presented hereafter.

We claim:

1. Method of reducing hair growth and/or hair thickness comprising:
    formulating a cosmetic composition comprising a lysine-based advanced glycation end product chosen from compounds corresponding to the following formulae—

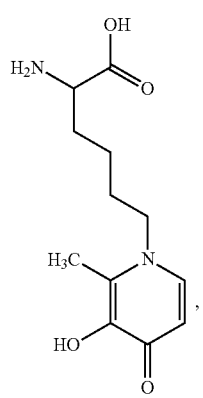

15

-continued

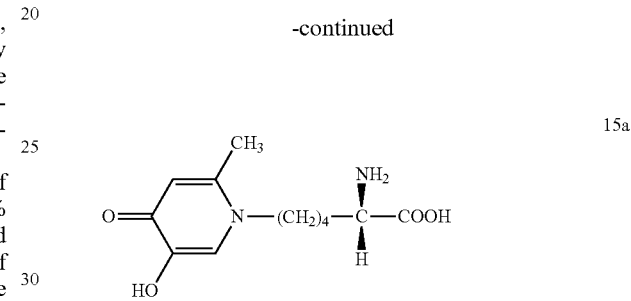

15a or mixtures thereof, and topically applying to a subject in need of reducing hair growth and/or hair thickness the cosmetic composition comprising the lysine-based advanced glycation end product to skin and/or hair.

2. Method according to claim 1 wherein the cosmetic composition decreases cellular division activity of fibroblasts, thereby inhibiting proliferation of hair growth.

3. Method according to claim 1 wherein the cosmetic composition inhibits the release of Hepatocyte Growth Factor and/or Keratinocyte Growth Factor, thereby inhibiting proliferation of hair growth.

4. Method according to claim 1 wherein the lysine-based advanced glycation end product is maltosine (formula 15) and the composition is an anti-hair growth agent.

5. Method according to claim 1 wherein the lysine-based advanced glycation end product(s) is present in the composition in an amount of 0.00001 to 15 wt. %, based on total weight of the composition.

6. Method according to claim 1 wherein the composition is in the form of a balm, tablet, lotion, cream, emulsion, suspension, milk, paste, a gel, foam or spray.

* * * * *